United States Patent [19]
Ross et al.

[11] 3,966,411
[45] June 29, 1976

[54] ANALYSIS FOR NITROGEN COMPOUNDS BY GAS CHROMATOGRAPHY

[76] Inventors: William D. Ross, 9060 Concord Road, R.R. 3, Eaton, Ohio 45320; Robert E. Sievers, 2628 N. Emerald Drive, Fairborn, Ohio 45324

[22] Filed: Apr. 8, 1975

[21] Appl. No.: 566,157

[52] U.S. Cl. .......................... 23/230 R; 23/230 M; 23/232 R; 23/232 C; 23/232 E; 252/408
[51] Int. Cl.² ................. G01N 31/08; G01N 31/10; G01N 33/18
[58] Field of Search .......... 23/230 R, 232 R, 232 C, 23/230 M, 232 E; 252/408

[56] References Cited
OTHER PUBLICATIONS

Grubner et al., "Sensitive Gas Chromatographic Detection of Nitrogen Dioxide", Anal. Chem., vol. 45, No. 6 pp. 944–947 (May 1973).
Morrison and Boyd, "Organic Chemistry," pp. 221, 237–239, 263 (1965).
Bond, Jr., "Gravimetric Determination of Styrene as Styrene Nitrosite," Anal. Chem., vol. 19, No. 6, pp. 390–392 (June 1947).

*Primary Examiner*—Morris O. Wolk
*Assistant Examiner*—Barry I. Hollander
*Attorney, Agent, or Firm*—Joseph E. Rusz; Cedric H. Kuhn

[57] ABSTRACT

The qualitative and quantitative analysis of nitrogen-containing compounds is accomplished by contacting in the presence of an acid a sample containing such a compound with an aromatic hydrocarbon, thereby converting the compound to a stable nitrogen-containing aromatic hydrocarbon. The sample now containing the nitrated aromatic hydrocarbon is then introduced in a carrier gas stream into a chromatographic column. The effluent stream from the column is passed through a gas chromatography detector, and the detector signal response obtained is compared with that produced by known amounts of a reference calibration sample.

19 Claims, 6 Drawing Figures

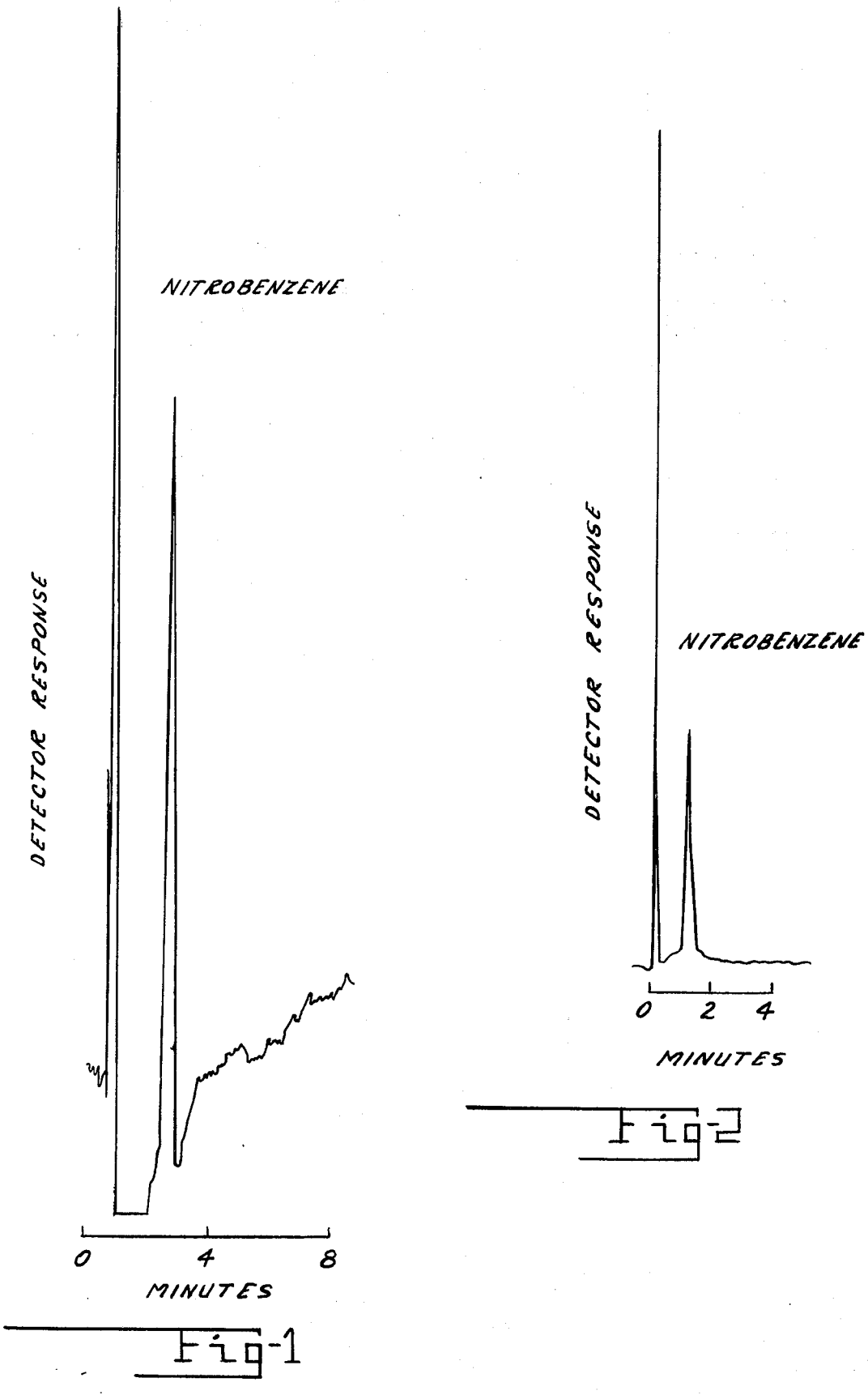

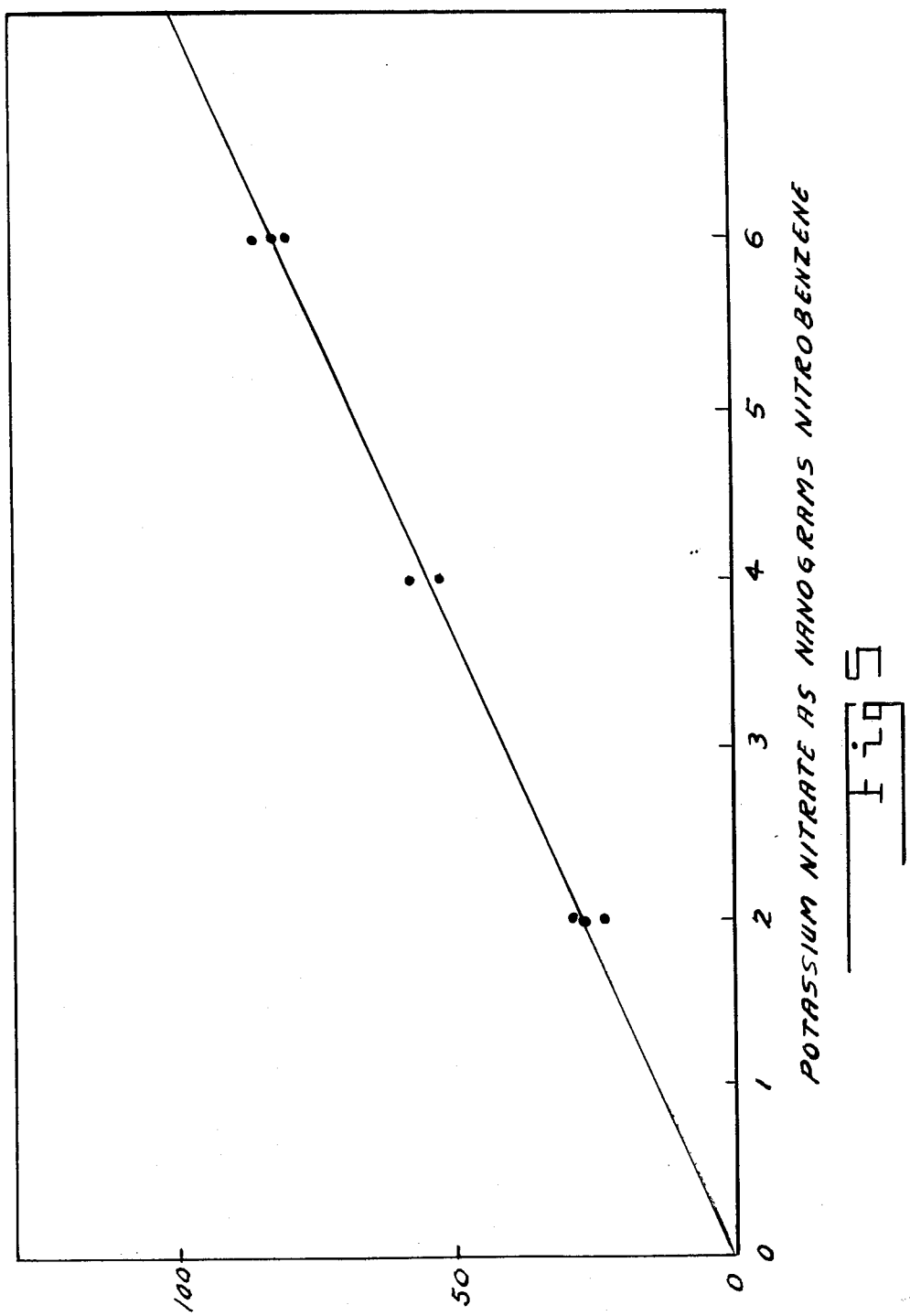

ANALYSIS FOR NITROGEN COMPOUNDS BY GAS CHROMATOGRAPHY

RIGHTS OF THE GOVERNMENT

The invention described herein may be manufactured and used by or for the Government of the United States for all governmental purposes without the payment of any royalty.

FIELD OF THE INVENTION

This invention relates to a process for analyzing for nitrogencontaining compounds by gas chromatograpy. In a more specific aspect, the invention relates to a process for the quantitative analysis of oxides of nitrogen in ambient air and nitrates and nitrites in an aqueous medium and in aerosols.

BACKGROUND OF THE INVENTION

Gas chromatography is a well known technique that is extensively used in quantitative analysis. However, in analyses involving nitrogen compounds, particularly nitrogen oxides, gas chromatography has provided results that are unreliable. Oxides of nitrogen, expecially nitrogen dioxide, are very reactive and at trace levels tend to be irreversibly absorbed, and thereby lost, on surfaces of storage containers, transfer lines, column packing materials, and the like. As a consequence the integrity of samples containing nitrogen oxides is often questionable, especially after storage or transfer is attempted.

Because of the concern in recent years of the impact of nitrogen oxides upon the environment, it has become important to provide an accurate and reliable method for their analysis. A widely used method for analysis of nitrogen oxides is based on chemiluminescence. While this technique is quite sensitive, it has a definite drawback in that it must be calibrated with mixtures of trace levels or reactive, difficult to store oxides of nitrogen. The accuracy with which these supposedly "standard" mixtures can be prepared is not very high and the integrity of standard gases after storage and transfer is often in question.

O. Grubner and A. S. Goldin in Analytical Chemistry, 45, 944 (May 1973), describe work in which styrene was used as a gas phase reactant with nitrogen dioxide. Five chromatographic peaks were observed. The authors concluded that the five peaks were not nitrated styrene derivatives but were probably cleaved fragments of the styrene because their retention times were shorter than styrene itself. When more than three products are formed, it is difficult, if not impossible, to make quantitative measurements because each compound produces a different size response in the chromatographic detector and small changes in reaction conditions can cause large changes in the ratios of the products produced. The authors state that they also studied reactions between nitrogen dioxide and benzene, toluene, xylene, pentene, 1,1-dimethylhydrazine and triethanolamine. However, they found that with their method only the reaction with xylene produced significant quantities of compounds that could be detected by an electron capture detector.

It is an object of this invention to provide an improved process for the qualitative and quantitative analysis of nitrogencontaining compounds.

Another object of the invention is to provide a gas chromatographic process for analysis of oxides of nitrogen in ambient air and nitrates and nitrites in an aqueous medium and in aerosols.

Other objects and advantages of the invention will become apparent to those skilled in the art upon consideration of the accompanying disclosure and the drawing, in which:

FIG. 1 is a chromatogram of the reaction product of $HNO_3$ and benzene;

FIG. 2 is a chromatogram of the reaction product of $KNO_3$ and benzene;

FIG. 5 is a calibration curve prepared by an alternative method; and

SUMMARY OF THE INVENTION

Figure 3:
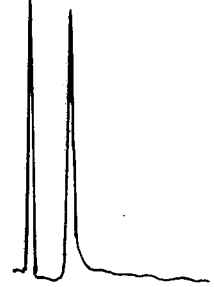
FIG. 3 is a chromatogram of nitrobenzene quantitatively diluted with benzene as a calibration reference.

The present invention resides in a process for the qualitative and quantitative analysis of a nitrogen-containing compound or an aromatic compound by converting the compound into a stable, volatile compound which can be detected with great sensitivity by a gas chromatography detector.

In one embodiment of the invention, a sample comprising a nitrogen-containing compound, such as nitric acid, a salt of nitric acid, the oxidation products of an organic nitrogen-containing compound or the oxidation products of gaseous oxides of nitrogen, is mixed with an aromatic compound. The nitrogen-containing compound reacts with the aromatic compound, thereby converting the former compound to a nitro-aromatic compound. A sample of the reaction mixture containing the newly formed nitro-aromatic compound is then passed through a chromatographic column and thence through a chromatography detector, particularly an electron capture detector. By comparing the detector signal response with the signal response produced by a reference calibration sample, i.e., a sample containing a known amount of the nitro-aromatic compound, the amount of nitrogen-containing compound is determined. More specifically, the determination is made by measuring the heights of or areas under the peak or peaks of the chromatograms representative of the nitro-aromatic compound and multiplying the amount of nitro-aromatic compound contained in the reference sample by the ratio of the peak heights or areas of the unknown to the peak heights or areas of the reference sample.

It is also within the scope of the invention to pass the sample containing the nitrogen compound directly through the electron capture detector without prior passage through the chromatographic column. This procedure can be followed when it is known that the sample does not contain compounds or impurities that will interfere with the response of the detector to the nitro-aromatic compound.

Exemplary nitrogen-containing compounds that can be analyzed for in accordance with this invention include nitrogen dioxide, nitric acid, and salts of nitric acid such as sodium nitrate and potassium nitrate. Also, organic nitrogen-containing compounds can be analyzed for by first converting them by oxidation to organic compounds containing a nitro group or by oxidation to nitrates. Examples of such compounds include heterocyclic compounds, such as pyridine, pyridol, pyridone and quinoline, nitrosamines, such as methylnitrosamine, diethylnitrosamine, phenylnitrosamine, diphenylnitrosamine and phenylethylnitrosamine, amino acids, and proteins. Furthermore, the present process can be used to analyze for nitrous oxide, nitric oxide, and nitrites by first oxidizing the compounds to nitrogen dioxide or to the nitrate as appropriate.

The amount of nitrite in admixture with a nitrate can also be determined by first analyzing for the amount of nitrate in the mixture. Thereafter, the nitrite in the mixture is oxidized to the nitrate after which the amount of nitrate is determined. The difference in the values of the two determinations is the amount of nitrite contained in the mixture.

Aromatic compounds that can be reacted with the nitrogen containing compounds to provide nitroaromatic compounds have the following formula:

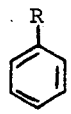

, where R is hydrogen, alkyl, alkoxy, hydroxy or amino. The alkyl and alkoxy groups contain from 1–10, preferably 1 to 4, inclusive, carbon atoms. Examples of compounds corresponding to the foregoing formula include benzene, toluene, ethylbenzene, t-butylbenzene, anisole, ethoxybenzene, butoxybenzene, phenol, aniline, and the like. In selecting an aromatic compound, it is important to choose one that forms no more than three isomers when reacted with the nitrogen-containing compound. When more than three products are formed, it is difficult, if not impossible, to make quantitative measurements because each product produces a different size response in the chromatographic detector and small changes in reaction conditions can cause large changes in the ratio of the products formed. It is necessary to know every product formed and its relative response factor. Identification of each compound would have to be made by an independent technique (such as mass spectrometry or from retention times) and measurements of the relative response factors by using pure samples of each of the compounds would also be necessary for accurate determinations. Because only a single product, namely, nitrobenzene is formed when benzene is employed, it is preferred to use benzene as the aromatic compound. Thus, with benzene only one chromatographic peak is formed, a condition that increases the accuracy of the quantitative determinations.

The temperature and time conditions at which the nitrogencontaining compounds and the aromatic compounds are reacted can vary within rather wide limits. In general, the reaction is carried out under conditions such that there is substantially a 100 percent conversion of the nitrogen-containing compound into one or more, but not more than three, stable, volatile nitro-aromatic compounds which can be detected with great sensitivity by chromatography detectors. Usually, the temperature ranges from about room temperature to 150°C while the reaction period varies from about 30 seconds to 2 hours, preferably from about 5 to 30 minutes.

The process of this invention makes possible the quantitative analysis of samples containing minute amounts of nitrogen compounds. Thus, amounts in the picogram range can be determined by the present process, determinations that have not been previously feasible with any degree of accuracy. Since the amount of nitrogen compound present in a sample is unknown, the exact amount of the aromatic compound to be added in any particular analysis cannot be positively delineated, nor is it necessary to do so. As a general proposition, an amount is added that is sufficient to result in substantially 100 percent conversion of the nitrogen compound into one or more, but not more than three, nitro-aromatic compounds. The amount of added aromatic compound is usually in excess of that required to complete the conversion and can be readily determined by one skilled in the art. The use of an excess amount of the aromatic compound is permissible because the compound does not produce a chromatography peak that interferes with the peak or peaks of the nitro-aromatic compound or compounds.

In carrying out the process of this invention, it is important that the reagents used be of high purity. In particular, the aromatic compound should be as free as possible of any nitro-aromatic compound, for otherwise an incorrect analysis will be obtained. To determine if any appreciable amount of a nitro-aromatic is present, prior to use the aromatic compound is passed through the chromatographic column and detector. If a peak for a nitro-aromatic compound shows up on the chromatogram and it has a considerable height, e.g., greater than 15 millimeter, the batch is treated, e.g., by fractional distillation, to remove the nitro-aromatic. However, if the peak is small, e.g., less than 15 millimeters, the aromatic compound can be used, in which case the peak height is subtracted from the height of the peak subsequently obtained from the unknown.

In conducting the present process, especially when using benzene, the preferred aromatic compound, it is important to acidify the solution containing the nitrogen compound with an acid, such as sulfuric or sulfurous acid. The acid catalyst accelerates the reaction and ensures that the conversion to nitrobenzene is highly reproducible and, as nearly as possible, approaches 100 percent. The reactions involved when analyzing for nitric acid and using benzene as the aromatic compound is shown by the following equations:

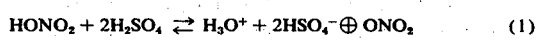

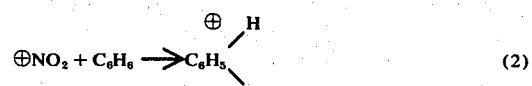

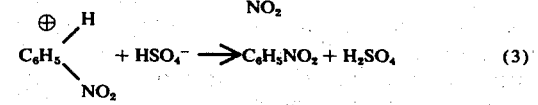

The acid catalyst is believed to accelerate reactions to form nitro organic products because it increases the concentration of the nitronium ion, $NO_2^+$, which attacks aromatic rings because of its electrophilic character.

In the foregoing discussion of the present process, aromatic compounds are employed as reactants to form sensitively and selectively detected products from traces of nitrogen compounds. In another embodiment of the invention, nitric acid is used as a reactant to form easily detected products from aromatic hydrocarbons that are of themselves difficult to detect. For example, traces or even substantial amounts of benzene cannot be detected by electron capture detectors, and toluene is similarly insensitive to detection.

In carrying out this embodiment of the invention, the aromatic hydrocarbon to be analyzed for is contacted with an excess of nitric acid. As a result of this contacting, nitration of the aromatic hydrocarbon occurs. The reaction conditions described hereinbefore can also be employed, and acid catalysts, such as sulfuric acid, can be used to accelerate the reactions. To facilitate handling, the aromatics being analyzed can be dissolved in an inert solvent, e.g., a paraffinic hydrocarbon such as hexane or octane. As previously described, samples of the reaction products are passed through a chromatographic column and then through a chromatography detector. Or if a separation is unnecessary, the samples can then be passed directly through the detector.

The provision of a process for analysis of aromatics, such as benzene and toluene, is important in characterizing pollutant emissions and various fuels. In particular, because they are carcinogenic pollutants, the process fulfills a need for a sensitive method for analysis of polynuclear aromatic hydrocarbons, such as benzo(a)-pyrene.

The procedure followed in the separation of the components of a mixture by gas chromatography is well known and is described in the literature. A chromatographic system conventionally comprises a chromatographic column which can be in the form of stainless steel, copper, glass, aluminum or Teflon tubing. Prior to use the column is packed with a composition that constitutes the stationary phase and comprises a particulate support material, such as silanized diatomaceous earth or glass beads, coated with a silicone oil or a hydrocarbon such as squalane or Apiezon L (J. G. Biddle Co.). Other compositions that can serve as the stationary phase are commercially available. Thereafter, the packed column is connected to a gas chromatograph. The chromatograph is conventionally provided with an injection port, a heating means, a thermostat, a detector, and a recording means. While flame ionization detectors, alkali metal nitrogen detectors, and mass spectrometric detectors can be used, an electron capture detector is preferred because it gives the greatest sensitivity and selectivity.

Initially, the column is conditioned by passing a carrier gas through the column for a period of time sufficient to remove any trace impurities from the column. The period of time required to condition a column usually ranges from about 4 to 72 hours. An inert gas, such as nitrogen, helium or argon, is used as the carrier gas. During the conditioning procedure, the column is heated to about 5° to 15°C above the temperature at which it is intended to operate the column during the separation process.

After the column is conditioned, a sample of the reaction mixture containing a nitro-aromatic compound is introduced into the column through the injection port. The injection port is preheated to a temperature high enough to vaporize the sample, and this temperature will necessarily depend upon the particular sample that is introduced. During operation of the column, the carrier gas is injected into and flowed through the column at a constant rate, thereby sweeping the vaporized sample through the column. The temperature of the column is such as to maintain a vapor phase therein and to cause reasonably rapid elution. While the sample is in the column, an equilibrium exists between the stationary phase and the vapor phase so that molecules are continually being transferred from the vapor phase to the liquid phase and vice versa. While molecules are in the vapor or moving phase, they are swept further through the column. When molecules are in the stationary liquid phase, as the name implies, their progress through the column is impeded or delayed. As a result of this phenomenon, different molecules have different retention times in the column. The actual retention times of a nitro-aromatic compound and any impurities or other compounds in the sample is determined by means of the detector which is operatively connected to a recording system. By means of the recording system, a graphical indication (chromatogram) of the retention times is obtained. By comparing retention times on the chromatogram with the known retention time of nitro-aromatic compounds, the unknown nitro-aromatic compound in the sample can be identified. Furthermore, as explained hereinbefore, the amount of nitro-aromatic compound in the sample can be determined by multiplying the known amount of the nitro-aromatic in a calibration sample by the ratio of the height of the peak of the unknown sample to the height of the peak of the known calibration sample. For more accurate results, calibration curves are usually constructed by measuring the peak heights or areas of several known standards in the concentration range expected for unknown. A plot of concentration vs. peak height or peak area is made. A smooth line or curve is drawn through the known values. The concentration of unknown samples is determined subsequently from the calibration curve in the conventional manner.

A more complete understanding of the invention can be obtained by referring to the following illustrative examples which are not intended, however, to be unduly limitative of the invention.

EXAMPLE I

In the runs of this and succeeding examples (unless otherwise noted) the instrument used was a Hewlett-Packard Research Chromatograph Model 402. The chromatographic column was a glass tube, 1.2 meters long and 3.0 mm inside diameter, packed with 3.8 weight percent UC-W98 silicone fluid (Union Carbide) supported on Gas Chrom Z silanized diatomaceous earth (80–100 mesh) (Applied Science Laboratory). The column temperature was 100°C, and the flow rate of nitrogen carrier gas through the column was 60 ml/min, supplemented with a purge gas stream through the $Ni^{63}$ electron capture detector of 90% argon-10% methane.

Runs were carried out in which standard solutions of nitric acid were analyzed. The procedure followed was to add 10 ml of concentrated sulfuric acid to a 200 ml, round-bottom flask. Thereafter, 25 ml of benzene was added to the flask. The reagents were shaken for 5 minutes, and a 1-$\mu$l aliquot of the benzene from the benzene layer which separated after standing was injected into the chromatographic column. The chromatogram obtained was examined for the presence of indications of any nitrobenzene. If blank nitrobenzene was found that produced peak heights greater than 15 mm, the benzene was discarded and fresh benzene added and the process was repeated. If the blank peak was less than 15 mm, the peak height of the nitrobenzene was subtracted from the peak height subsequently obtained from the unknown.

One ml of the "unknown" aqueous sample of concentrated nitric acid which had been diluted by a factor of 100,000 was added to the flask containing benzene and sulfuric acid. The reagents were shaken for 5 minutes. Five 1-$\mu$l aliquots of the benzene layer were analyzed. The peak heights obtained were compared to the peak heights of standard nitrobenzene. Standard nitrobenzene solutions were prepared by quantitative dilution of pure nitrobenzene with benzene. A peak height of 30 mm was obtained which, when compared with the peak heights of the standard nitrobenzene solutions, indicated that the unknown aqueous sample contained $1.0 \times 10^{-12}$ ml of concentrated nitric acid.

Another run was conducted in which essentially the same procedure described above was followed. The instrument used was a Hewlett-Packard F&M Model 810 Research Chromatograph. The column, which was 1 meter long and had an inside diameter of 2.0 mm, was packed with 10% SE-30 silicone (General Electric) (a polydimethylsiloxane) coated on Chromosorb W which had been acid-washed and silanized. The column temperature was 120°C, and the flow rate of 10% methane-90% argon through the titanium tritide detector was 60 ml/min. The detector temperature was 180°C.

In FIG. 1 there is shown the chromatogram of the reaction product of $HNO_3$ and benzene that was obtained in this run.

EXAMPLE II

Runs were conducted in which a standard solution of potassium nitrate was analyzed. A procedure similar to that described in Example I was followed. The reaction mixture was heated at 68°C, and a Teflon stirring bar was used to agitate and mix the reagents. The only difference observed in the results obtained between heating while stirring and shaking the sample at ambient was the expected more rapid rate of reaction. Consistent peak heights were obtained in less than one minute of reaction time with the heated sample. Greater than one minute but less than 5 minutes was required to obtain consistent peak heights when no heating was used. The analyses indicated that the unknown sample contained $1.07 \times 10^{-5}$g $KNO_3$ per ml. FIG. 2 is a chromatogram of the reaction product of potassium nitrate and benzene.

Figure 4:
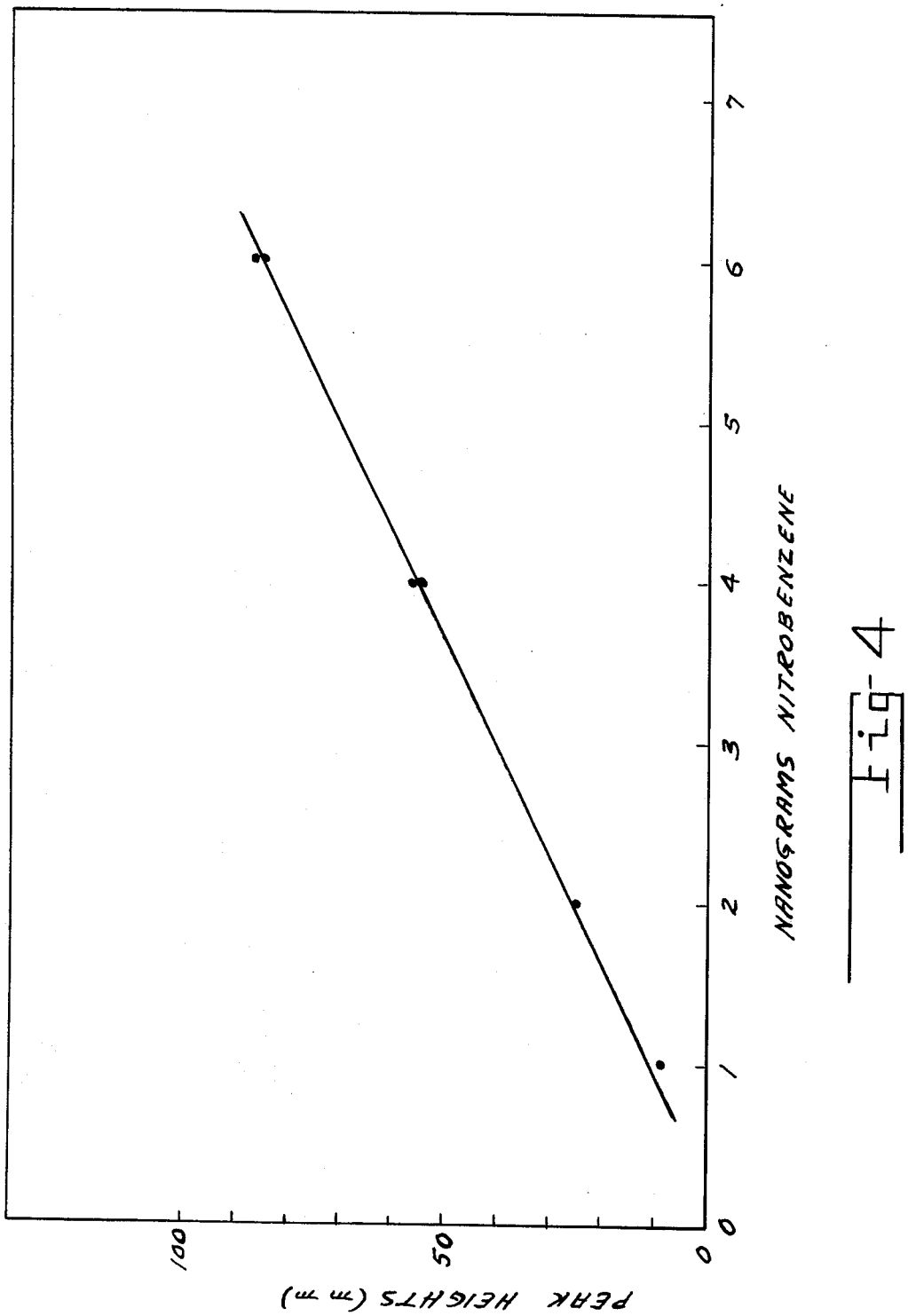
FIG. 4 is a calibration curve prepared by injecting several known amounts of nitrobenzene in benzene.

In determining the amount of $KNO_3$ in the unknown sample, several methods can be followed in obtaining a calibration reference or curve. FIG. 3 is a chromatogram of nitrobenzene quantitatively diluted with benzene as a calibration reference. FIG. 4 is a calibration curve prepared by injecting several known amounts of nitrobenzene in benzene. FIG. 5 shows an alternative method of calibration. In this method, weighed amounts of potassium nitrate dissolved in water at the ppm or lower levels are subjected to the same treatment as the unknown samples and the results are plotted as shown in FIG. 5. The following instrument conditions were used: Instrument, Hewlett-Packard Model 402 Research Chromatograph; column, 1.2 meter × 2 mm i.d., packed with 3.8% Union Carbide W 98 silicone on Diaport S; column temperature, 100°C; flow rate of 10% methane-90% argon through the $Ni^{63}$ electron capture detector; and detector temperature, 215°C. Detector responses vary with varying detector pulse intervals. In these experiments 5 microsecond pulse intervals were used but 50 microsecond intervals provide more sensitive response.

EXAMPLE III

A reaction efficiency study was conducted on a standard solution of potassium nitrate. The efficiency study was performed by comparing the chromatograms obtained by injecting aliquots of a standard solution of nitrobenzene with those obtained by reaction of the acidified $KNO_3$ solutions with benzene. Five runs were carried out, and the following data were obtained:

| Sample | | % Recovery |
|---|---|---|
| A | | 96 |
| B | | 112 |
| C | | 113 |
| D | | 95 |
| E | | 95 |
| | Mean | 102 |

The foregoing data show that the formation of nitrobenzene by reacting $KNO_3$ with benzene is quantitative under the conditions used.

EXAMPLE IV

A series of runs was conducted in which nitrogen dioxide entrapped in absorbing solutions of sulfuric acid was analyzed in accordance with the present invention. The procedure described hereinafter was followed in making the analyses.

A 2-liter collection flask was carefully cleaned, after which 25 ml of concentrated sulfuric acid was added. Ten milliliters of benzene was then added and the flask was shaken for 10 minutes to remove potential impurities in the sulfuric acid. The benzene was analyzed by gas chromatography for the presence of nitrobenzene. If no blank peak was evident or if it was very small, the benzene was decanted and discarded.

The flask containing the absorbing solution was then evacuated, and the pressure and temperature were recorded. The flask was then opened to the environmental area under investigation after which it was closed. The flask was shaken for 15 minutes on a "wrist action" shaker (Burrel Corp., Pittsburgh) and permitted to stand for at least 16 hours. After standing the flask was again shaken for 15 minutes.

A 200-ml round-bottom flask was prepared by adding 25 ml of concentrated sulfuric acid and 10 ml of benzene. The benzene layer was checked by gas chromatography for blank nitrobenzene. If appreciable amounts were found, it was discarded and replaced with a fresh aliquot of benzene.

The entire contents of the collection flask was carefully transferred to the reaction flask. The flask was not shaken for a 10 minute period because of exothermic heating. It was then shaken for 5 minutes. The benzene was carefully decanted and five 1-$\mu$l samples were analyzed by gas chromatography as described hereinbefore.

An aliquot of a $KNO_3$ standard solution, which is equivalent to 250 ppm of $NO_2$, was allowed to react with benzene in the presence of concentrated sulfuric acid by the same procedure as described above. The chromatographic calibration was established by analyzing the reaction mixture by gas chromatography.

An unknown ambient air sample and a sample from auto exhaust was subjected to the above-described analytical procedure. The amount of $NO_2$ present in each sample was determined by comparison of the nitrobenzene peak heights with those obtained from the standard aqueous KNO₃ solution.

Figure 6:
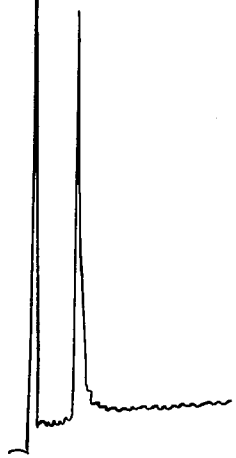
FIG. 6 is a chromatogram of the reaction product of $NO_2$ and benzene.

FIG. 6 is a chromatogram of the reaction product of NO₂ and benzene, using the same instrument conditions given in Example II.

In the foregoing example, an aqueous solution of sulfuric acid was used as the absorbing solution. It is within the scope of the invention to add hydrogen peroxide or other oxidizing agents to the dilute absorbing solution to facilitate oxidation of any nitric oxide contained in the sample without interfering in the chromatographic procedure. Furthermore, other absorbing solutions can be used to trap oxides of nitrogen from the air and convert them to aqueous species, particularly the nitrate ion. For example, basic solutions, such as those containing sodium hydroxide or triethanolamine, absorb nitrogen dioxide from the air.

EXAMPLE V

Runs were conducted for the purpose of establishing the detection limits for nitrobenzene by electron capture. Standard solutions were made that consisted of 1 × 10⁻⁸ ml nitrobenzene per ml of benzene. One microliter of this solution produced a peak 57 mm high. Two-tenths of a microliter produced a peak 15 mm high; this sample contained 2 × 10⁻¹² ml of nitrobenzene. These data demonstrate that the sensitivity of the present process is sufficient to detect and measure nitrogen-containing compounds at lower levels and with greater accuracy, reliability and convenience than is possible by other methods.

As seen from the foregoing example, the present process is effective for analyzing for trace amounts of nitrogen-containing compounds. Thus, the process is particularly useful in the detection of nitrogen compounds that may be a hazard to the environment. For example, nitric acid, potassium nitrate and nitrogen dioxide are representative of classes of compounds that are environmental problems, e.g., HNO₃ from industrial mists and in water effluents, NO₂ from auto and aircraft exhausts, and KNO₃ in water effluents from industrial processes and agricultural run-off.

In general, other methods for nitrate analysis of aqueous samples of oxides of nitrogen in gases are inferior to the present process. As previously mentioned, one method now widely used for NO₂ analysis is based on chemiluminescence. While this method is quite sensitive, it has a definite drawback in that it must be calibrated with trace levels of reactive, difficult-to-store oxides of nitrogen. In the practice of the present process, such standard gases are not required since calibration can be accomplished by comparison with accurately prepared and stable solutions of samples of either potassium nitrate in water or nitrobenzene in benzene, or both. Pure samples of potassium nitrate or nitrobenzene can be readily weighed and easily diluted to the appropriate concentration to the levels actually being measured. Since the conversion of nitrate to nitrobenzene is quantitative, either calibration system can be used.

As will be evident to those skilled in the art, modifications of the present invention can be made in view of the foregoing disclosure without departing from the spirit or scope of the invention.

We claim:

1. A process for the quantitative analysis of nitrogen-containing compounds which comprises mixing a sample comprising a nitrogen-containing compound selected from the group consisting of nitric acid, a salt of nitric acid, the oxidation products of an organic nitrogen-containing compound and nitrogen dioxide with an aromatic compound having the following formula:

where R is hydrogen, alkyl, alkoxy, hydroxy or amino; reacting with nitrogen-containing compound with the aromatic compound in the presence of sulfuric or sulfurous acid, thereby converting the nitrogen-containing compound to a nitro-aromatic compound; and passing a sample of the resulting reaction mixture containing the nitro-aromatic compound through a chromatography detector.

2. The process according to claim 1 in which the sample of the resulting reaction mixture is passed through a chromatography detector which is an electron capture detector.

3. The process according to claim 2 in which the signal response of the electron capture detector is compared with the signal response produced by a sample containing a known amount of the nitroaromatic compound.

4. The process according to claim 1 in which the sample of the reaction mixture is vaporized; the vaporized sample is swept through a chromatographic column by a carrier gas injected thereinto, the temperature of the column being such as to maintain a vapor phase therein; and passing the effluent from the column through the chromatography detector.

5. The process according to claim 4 in which the effluent from the column is passed through a chromatography detector which is an electron capture detector.

6. The process according to claim 5 in which the signal response of the electron capture detector is compared with the signal response produced by a sample containing a known amount of the nitroaromatic compound.

7. The process according to claim 6 in which a sample comprising an aqueous solution of nitrogen dioxide in sulfuric acid is mixed with benzene, and the nitrogen dioxide and benzene are reacted in the presence of concentrated sulfuric acid, thereby converting the nitrogen dioxide to nitrobenzene.

8. The process according to claim 6 in which a sample comprising an aqueous solution of nitric acid is mixed with benzene, and the nitric acid and benzene are reacted in the presence of concentrated sulfuric acid, thereby converting the nitric acid to nitrobenzene.

9. The process according to claim 6 in which a sample comprising an aqueous solution of potassium nitrate is mixed with benzene, and the potassium nitrate and benzene are reacted in the presence of concentrated sulfuric acid, thereby converting the potassium nitrate to nitrobenzene.

10. The process according to claim 6 in which a sample comprising an aqueous solution of nitric acid is mixed with toluene, and the nitric acid and toluene are reacted, thereby converting the nitric acid to ortho-, meta- and para-nitrotoluene.

11. The process according to claim 6 in which a sample comprising an aqueous solution of nitric oxide in sulfuric acid is mixed with benzene, and the nitric oxide and benzene are reacted in the presence of concentrated sulfuric acid and hydrogen peroxide, thereby converting the nitric oxide to nitrobenzene.

12. A process for the quantitative analysis of aromatic compounds having the following formula:

where R is hydrogen, alkyl, alkoxy, hydroxy or amino; which comprises mixing a sample comprising the aromatic compound with an aqueous solution of nitric acid; reacting the aromatic compound with the nitric acid in the presence of sulfuric or sulfurous acid, thereby converting the aromatic compound to a nitro-aromatic compound; and passing a sample of the resulting reaction mixture containing the nitro-aromatic compound through a chromatography detector.

13. The process according to claim 12 in which the sample of the reaction mixture is vaporized; the vaporized sample is swept through a chromatographic column by a carrier gas injected thereinto, the temperature of the column being such as to maintain a vapor phase therein; and passing the effluent from the column through the chromatography detector.

14. The process according to claim 13 in which the effluent from the column is passed through a chromatography detector which is an electron capture detector.

15. The process according to claim 14 in which the signal response of the electron capture detector is compared with the signal response produced by a signal containing a known amount of the nitro-aromatic compound.

16. The process according to claim 15 in which a sample comprising benzene is mixed with an aqueous solution of nitric acid, and the benzene and nitric acid are reacted in the presence of concentrated sulfuric acid, thereby converting the benzene to nitrobenzene.

17. The process according to claim 15 in which a sample comprising toluene is mixed with an aqueous solution of nitric acid, and the toluene and nitric acid are reacted, thereby converting the toluene to ortho-, meta- and para-nitrotoluene.

18. A process for the quantitative analysis of oxides of nitrogen which comprises mixing a sample comprising an aqueous solution of oxides of nitrogen in sulfuric acid with benzene; reacting the oxides of nitrogen with the benzene in the presence of concentrated sulfuric acid and hydrogen peroxide, thereby converting the oxides of nitrogen to nitrobenzene; and passing a sample of the resulting reaction mixture containing nitrobenzene through a chromatography detector.

19. The process according to claim 18 in which the signal response of the chromatography detector is compared with the signal response produced by a sample containing a known amount of nitrobenzene.

* * * * *